(12) United States Patent
Park et al.

(10) Patent No.: US 8,356,519 B2
(45) Date of Patent: Jan. 22, 2013

(54) NON-CONTACT TYPE TRANSDUCER FOR ROD MEMBER HAVING MULTI-LOOP COIL

(75) Inventors: Chan Il Park, Gunpo Si (KR); Sun Ho Lee, Yongin Si (KR); Yoon Young Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 234 days.

(21) Appl. No.: 12/849,584

(22) Filed: Aug. 3, 2010

(65) Prior Publication Data

US 2011/0036172 A1 Feb. 17, 2011

(30) Foreign Application Priority Data

Aug. 12, 2009 (KR) .................. 10-2009-0074282

(51) Int. Cl.
*G01N 29/34* (2006.01)
*B06B 1/04* (2006.01)
(52) U.S. Cl. ............................... 73/649; 73/668
(58) Field of Classification Search .............. 73/649, 73/592, 668; 324/240, 201, 345
See application file for complete search history.

(56) References Cited

U.S. PATENT DOCUMENTS

| | | | | | |
|---|---|---|---|---|---|
| RE28,381 E | * | 4/1975 | Edson | ............................ | 318/118 |
| 3,924,451 A | * | 12/1975 | Drnevich | ....................... | 73/594 |
| 4,309,634 A | * | 1/1982 | Koroly et al. | .................. | 310/201 |
| 4,621,231 A | * | 11/1986 | Heinrich et al. | ............... | 324/142 |
| 5,699,875 A | * | 12/1997 | Dugan | ............................... | 182/3 |
| 6,522,128 B1 | * | 2/2003 | Ely et al. | ................... | 324/207.17 |
| 6,529,008 B1 | * | 3/2003 | Mohamed | ...................... | 324/345 |
| 7,463,112 B1 | * | 12/2008 | Groves | ............................. | 333/33 |
| 8,098,065 B2 | * | 1/2012 | Kwun et al. | ................... | 324/240 |

FOREIGN PATENT DOCUMENTS

| | | |
|---|---|---|
| KR | 1020050098580 A | 10/2005 |
| KR | 1020050102516 A | 10/2005 |

* cited by examiner

*Primary Examiner* — J M Saint Surin
(74) *Attorney, Agent, or Firm* — Kile Park Goekjian Reed & McManus PLLC

(57) ABSTRACT

Provided is a non-contact type transducer for performing modal testing or non-destructive diagnosis easily, that is, a non-contact type transducer by which even an inexperienced person may perform modal testing or non-destructive diagnosis without errors. The transducer includes a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member; and one or more magnets that are arranged to form a static magnetic field on the surface of the rod member, whereon the surface of the rod member a dynamic magnetic field is formed by the multi-loop coils in the direction parallel to the lengthwise direction of the rod member, even partially in a direction parallel to the lengthwise direction of the rod member.

18 Claims, 18 Drawing Sheets

NON-CONTACT TYPE TRANSDUCER FOR ROD MEMBER HAVING MULTI-LOOP COIL

CROSS-REFERENCE TO RELATED PATENT APPLICATION

This application claims the benefit of Korean Patent Application No. 10-2009-0074282, filed on Aug. 12, 2009, in the Korean Intellectual Property Office, the disclosure of which is incorporated herein in its entirety by reference.

BACKGROUND OF THE INVENTION

1. Field of the Invention

The present invention relates to a transducer capable of performing modal testing or non-destructive testing of a rod member, and more particularly, to a non-contact type transducer for performing structural diagnosis of a rod member by performing non-contact excitation of the rod member or detecting a signal propagating in the excited rod member.

The present invention is derived from the research performed as a part of the New Technology Research & Development Support Project carried out by Korea Engineering and Science Foundation and Seoul University Industry Academic Cooperation Foundation.

[Project Number: 2009-0083279, Title: Multi-Scale Paradigm for Creative Design of Multi-Physical Complex Structure System]

2. Description of the Related Art

When a machine device is being designed or checked, in many cases, modal testing may be performed to diagnose structural stability. Resonant damage and wear-off due to vibration caused by operation of a machine device may be prevented by obtaining information regarding natural frequency and mode shape through modal testing and designing the mechanical device in consideration of the information. Accordingly, structural stability of the machine device may be improved.

To perform modal testing for figuring out vibration characteristics of a member constituting a machine device, it is necessary to vibrate the member to be tested and to detect the vibration.

FIG. 1 is a diagram roughly showing a method of performing modal testing in the prior art.

As shown in FIG. 1, in the prior art, a member to be tested 2 is generally vibrated by a person using an impact hammer 80. Furthermore, a commercial accelerometer 70 is attached to the member to be tested 2 to detect signals transmitted through the vibrated member to be tested. However, in cases where a person vibrates a member to be tested, repeatability of the test cannot be guaranteed.

Therefore, demand for development of a method and an apparatus for uniformly vibrating a member to be tested and detecting the vibration during modal testing has risen.

Furthermore, in addition to modal testing, it is difficult to perform non-contact type structural diagnosis of a machine member through non-destructive testing. Especially, in cases when a machine member is already installed, it is difficult to perform contact type structural diagnosis, either because it is necessary to disassemble the machine member or because other machine members may interfere.

Therefore, a demand for development of a transducer capable of easily performing structural diagnosis has risen.

SUMMARY OF THE INVENTION

The present invention provides a non-contact type transducer for performing modal testing or non-destructive diagnosis easily, that is, a non-contact type transducer by which even an inexperienced person may perform modal testing or non-destructive diagnosis without errors.

According to an aspect of the present invention, there is provided a transducer including a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member; and one or more magnets that are arranged to form a static magnetic field on the surface of the rod member, whereon the surface of the rod member a dynamic magnetic field is formed by the multi-loop coils in the direction parallel to the lengthwise direction of the rod member, even partially in a direction parallel to the lengthwise direction of the rod member, wherein the rod member is formed of a conductor, an eddy current flowing on the surface of the rod member in a circumferential direction of the rod member is generated by adjusting currents flowing in the multi-loop coils, a force is applied to the rod member in a direction perpendicular to the lengthwise direction of the rod member due to the static magnetic field formed by the eddy current and the static magnetic field, when a wave vibrating in a direction perpendicular to the lengthwise direction of the rod member is transmitted along the rod member, an eddy current is generated in the circumferential direction of the rod member under the static magnetic field, and an electromotive force is formed in the multi-loop coil to form a magnetic field in a direction that is opposite to the direction in which a magnetic field formed by the eddy current is formed, to offset the magnetic field formed by the eddy current, and a vibration transmitted to the rod member may be detected by detecting the electromotive force.

The multi-loop coil is a figure-of-8 type coil including two looped coil portions, the two looped coil portions are arranged on top of the rod member in a line parallel to the lengthwise direction of the rod member, and directions in which the two looped coil portions are wound are different from each other.

The multi-loop coil includes three looped coil portions, the three looped coil portions are arranged on top of the rod member in a line parallel to the lengthwise direction of the rod member, and a direction in which a middle looped coil portion of the three looped coil portions is wound may be different from a direction in which the other two looped coil portions are wound.

The magnet is arranged at a center of the middle looped coil portion of the three looped coil portions and apart from the rod member, and a neutral plane between the N pole and the S pole of the magnet may be parallel to the rod member.

The static magnetic field may be formed by arranging two or more magnets such that opposite poles thereof face each other and the magnets are apart from each other in the lengthwise direction of the rod member.

The static magnetic field may be formed by two magnets, and the two magnets may be arranged such that neutral planes between the N poles and the S poles of the two magnets are parallel to the rod member, such that the S pole of one of the magnet faces the rod member, and such that the N pole of the other magnet faces the rod member.

According to another aspect of the present invention, there is provided a transducer including a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member; one or more magnets that are arranged to form a static magnetic fields on the surface of the rod member, whereon the surface of the rod member a dynamic magnetic field is formed by the multi-loop coils in a direction parallel to the lengthwise direction of the rod member, even partially in a direction parallel to the lengthwise direction of the rod member; and a conductive foil wound around the rod member to cover portions of the rod member facing the multi-loop coils, wherein an eddy current flowing on the surface of the rod member in the circumferential direction of the rod member is generated by adjusting currents flowing in the multi-loop coils, a force is applied to the rod member in a direction perpendicular to the lengthwise direction of the rod member due to the static magnetic field formed by the eddy current and the static magnetic field, when a wave vibrating in a direction perpendicular to the lengthwise direction of the rod member is transmitted along the rod member, an eddy current is generated in the circumferential direction of the rod member under the static magnetic field, and an electromotive force is formed in the multi-loop coil to form a magnetic field in a direction that is opposite to the direction in which a magnetic field formed by the eddy current is formed, to offset the magnetic field formed by the eddy current, and a vibration transmitted to the rod member may be detected by detecting the electromotive force.

According to another aspect of the present invention, there is provided a transducer including a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member; and a power source, which applies power to the multi-loop coil, so that the multi-loop coil forms a magnetic field, wherein the rod member is formed of a conductor, an eddy current flowing on the surface of the rod member in the circumferential direction of the rod member is generated by adjusting currents flowing in the multi-loop coils, and a force is applied to the rod member in a direction perpendicular to the lengthwise direction of the rod member due to the magnetic field formed by the eddy current and the magnetic field formed by the multi-loop coil.

The multi-loop coil is a figure-of-8 type coil including two looped coil portions, the two looped coil portions are arranged on top of the rod member in a line parallel to the lengthwise direction of the rod member, and directions in which the two looped coil portions are wound may be different from each other.

The multi-loop coil includes three looped coil portions, the three looped coil portions are arranged on top of the rod member in a line parallel to the lengthwise direction of the rod member, and a direction in which a middle looped coil portion of the three looped coil portions is wound may be different from a direction in which the other two looped coil portions are wound.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the term "multi-loop coil" refers to a coil including two or more looped coil portions electrically connected to each other. Furthermore, directions in which the looped coil portions are wound may be different from each other (e.g. clockwise and counterclockwise), and thus directions of magnetic fields formed around the looped coil portions when a current flows in the coil may be different from each other.

Furthermore, the term "rod member" refers to not only hollow members, such as pipes, tubes, and hollow shafts, but also various mechanical members having circular or elliptical cross-sections, such as rotation shafts and various other structural members.

Figure 1:
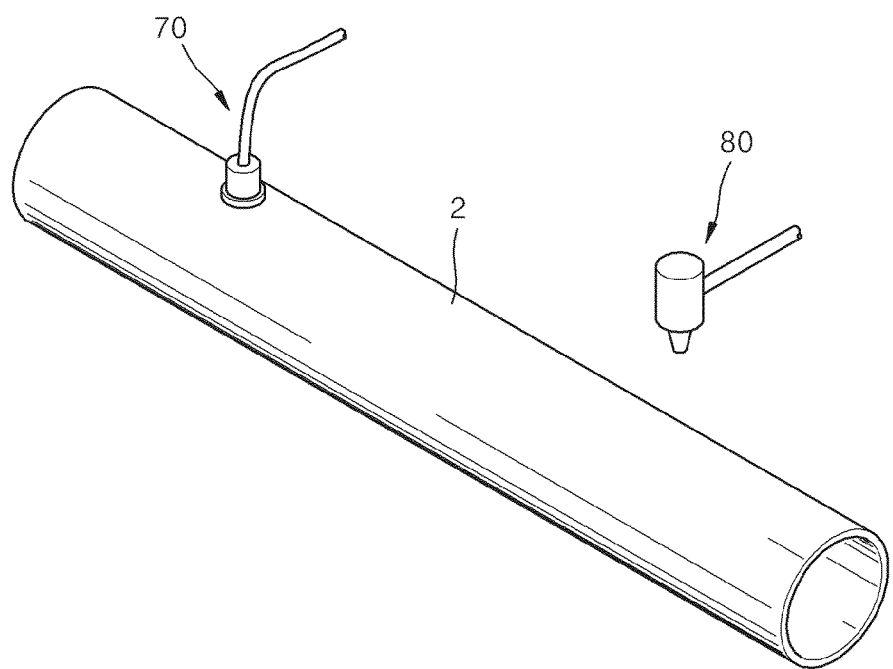
FIG. 1 is a diagram roughly showing a method of performing modal testing in the prior art.
Figure 2:
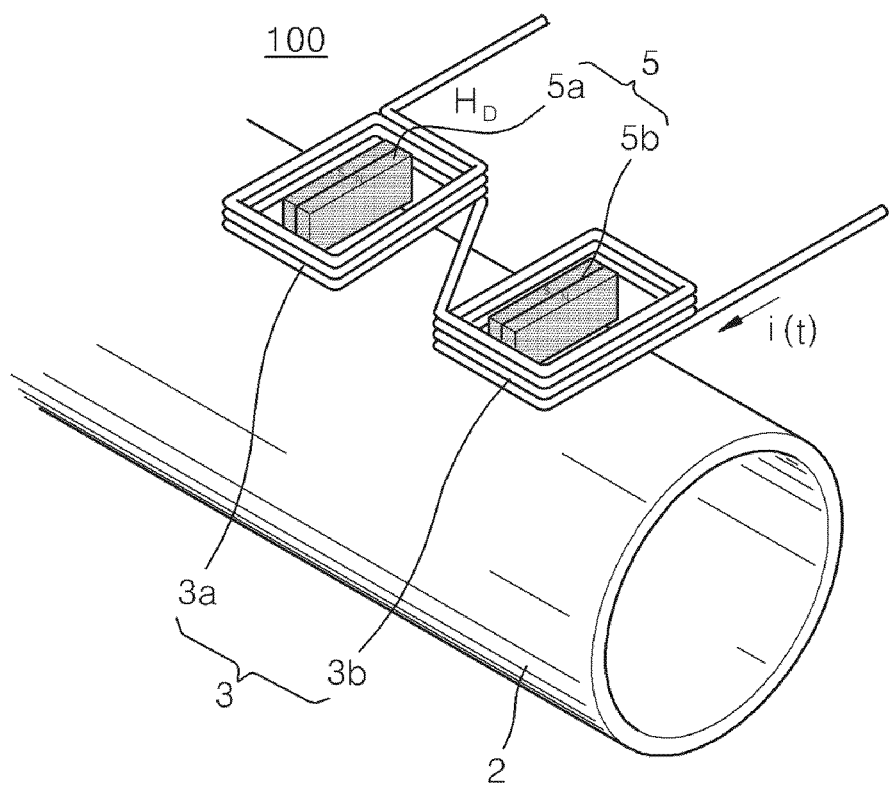
FIG. 2 is a schematic diagram of a transducer according to an embodiment of the present invention.

FIG. 2 is a schematic diagram of a transducer 100 according to an embodiment of the present invention.

The present embodiment provides a transducer that may be used with respect to metal rod members having electrical conductivity, and is directed to an electromagnetic acoustic transducer (EMAT) utilizing electromagnetic induction and Lorentz force.

As shown in FIG. 2, the transducer 100 according to the present embodiment includes a multi-loop coil 3 and a static magnetic field forming unit 5.

The multi-loop coil 3 of the present embodiment is a coil including two or more looped coil portions and directions in which the looped coil portions are wound may be different from each other. The multi-loop coil 3 is located at a location close to a location to be vibrated of a rod member 2, which is a member to be tested and is formed of a metal.

Figure 3:
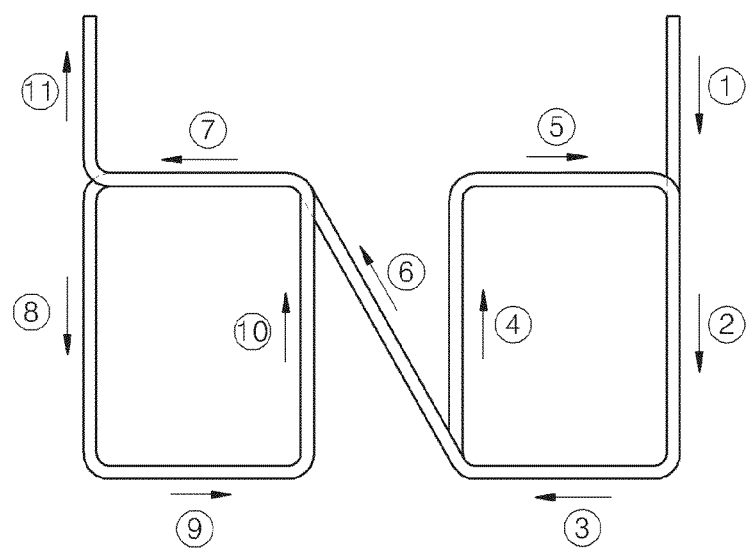
FIG. 3 is a diagram for describing a method of winding a multi-loop coil of the present invention.

FIG. 3 is a diagram for describing a method of winding the multi-loop coil 3 of the present embodiment.

As shown in FIG. 3, if a portion of the multi-loop coil 3 is wound clockwise in the order of ①, ②, ③, ④, and ⑤, then another portion of the multi-loop coil 3 across the portion ⑥ is wound counterclockwise in the order of ⑦, ⑧, ⑨, ⑩, and ⑪. In this case, when a current flows in a direction indicated by arrows in FIG. 3, directions of magnetic fields formed by the looped coil portions are different from each other. In other words, in FIG. 3, a magnetic field at a right looped coil portion is formed in a direction perpendicularly out of the FIG. 3, whereas a magnetic field at a left looped coil portion is formed in a direction perpendicularly into the FIG. 3. As a result, a magnetic field $B_D$ formed around the multi-loop coil 3 circulates from the inside of one looped coil portion to the inside of the other looped coil portion.

The looped coil portions of the multi-loop coil 3 of the present embodiment have substantially the same size, and the multi-loop coil 3 is installed over the rod member 2 in such a way that an imaginary line connecting the centers of the two looped coil portions is parallel to the lengthwise direction of the rod member 2.

The static magnetic field forming unit 5 forms a static magnetic field in a direction parallel to the lengthwise direction of the rod member 2. For example, as shown in FIG. 2, the static magnetic field forming unit 5 is formed of two permanent magnets 5a and 5b, and the two permanent magnets 5a and 5b may be arranged apart from each other and having opposite poles face each other. In this case, the two permanent magnets 5a and 5b may be arranged inside the looped coil portions of the multi-loop coil 3, respectively, or may be arranged outside the looped coil portions of the multi-loop coil 3.

Figure 4:
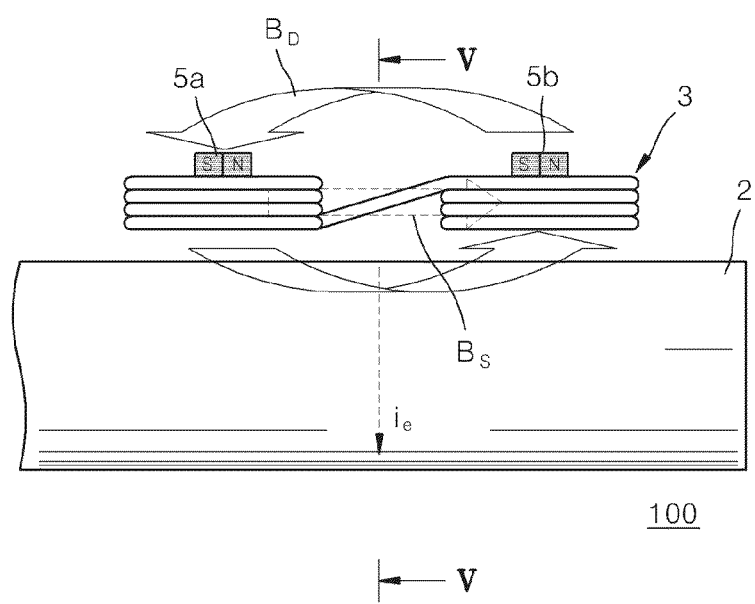
FIG. 4 is a side view of the transducer and the rod member to be tested shown in FIG. 2.

FIG. 4 is a side view of the transducer 100 and the rod member 2 to be tested according to the present embodiment shown in FIG. 2.

As shown in FIG. 4, the magnetic field $B_D$ around the multi-loop coil 3 is formed on the surface of the rod member 2 in a direction parallel to the lengthwise direction of the rod member 2, and a magnetic field $B_S$ formed by the static magnetic field forming unit 5 is also formed in a direction parallel to the lengthwise direction of the rod member 2.

In this case, when a current flowing in the multi-loop coil 3 increases, the intensity of the magnetic field around the multi-loop coil 3 increases, and thus an eddy current $i_e$ flows on the surface of the rod member 2, which is a conductor, as indicated with a dotted line in FIG. 4 to offset the increase of the intensity of the magnetic field, which increases due to electromagnetic induction.

Figure 5:
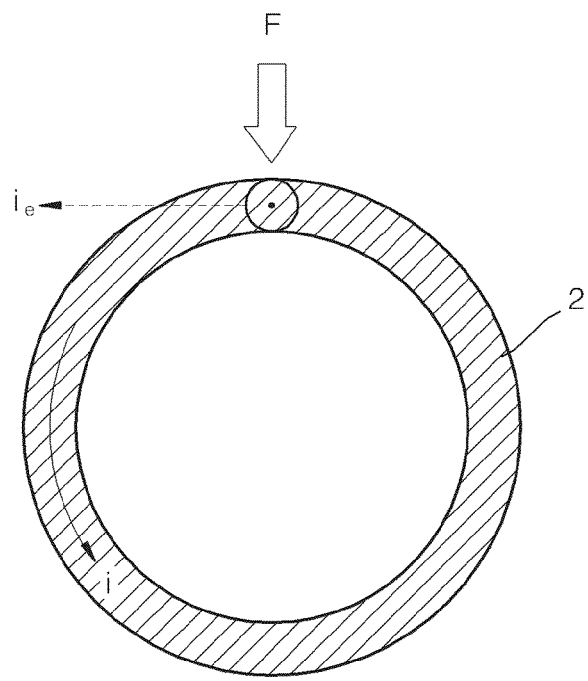
FIG. 5 is a sectional view obtained along a line V-V of FIG. 4.

FIG. 5 is a sectional view obtained along a line V-V of FIG. 4.

As shown in FIG. 5, in cases where the eddy current $i_e$ flows on the surface of the rod member 2 in a circumferential direction, a force F is applied at a location beneath the transducer 100 in a direction perpendicular to the lengthwise direction of the rod member 2 due to the eddy current $i_e$ and the static magnetic field $B_S$. The force F may act as an impact hammer would during modal testing in the prior art.

Figure 6:
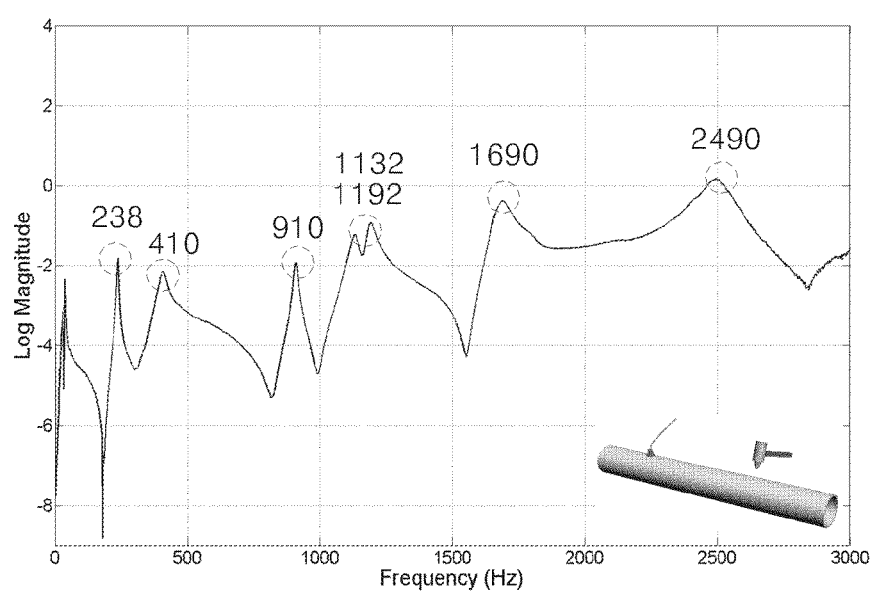
FIG. 6 is a graph of a frequency response function (FRF) obtained by performing modal testing with respect to a steel pipe by using an impact hammer.
Figure 7:
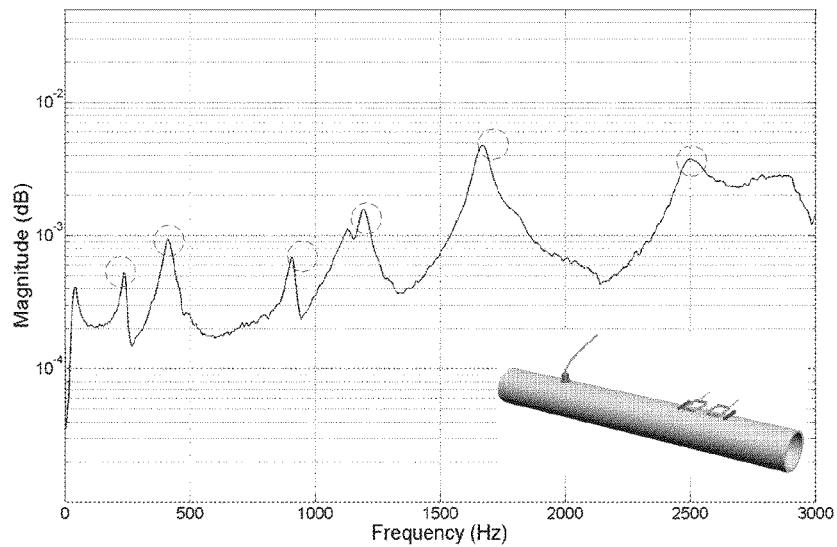
FIG. 7 is a graph of a FRF obtained by performing modal testing with respect to the same steel pipe by using a device having a transducer according to the present embodiment.

FIG. 6 is a graph of a frequency response function (FRF) obtained by performing modal testing with respect to a steel pipe by using an impact hammer, and FIG. 7 is a graph of a FRF obtained by performing modal testing with respect to the same steel pipe by using a device having a transducer according to the present embodiment.

The tested member was a steel pipe, of which the length is 900 mm, the average diameter is 76 mm, and the thickness is 1.6 mm. Natural frequencies obtained through modal testing in FIGS. 6 and 7 are almost identical to each other. Therefore, a transducer according to the present embodiment may be used as a transmitter for modal testing.

Figure 8:
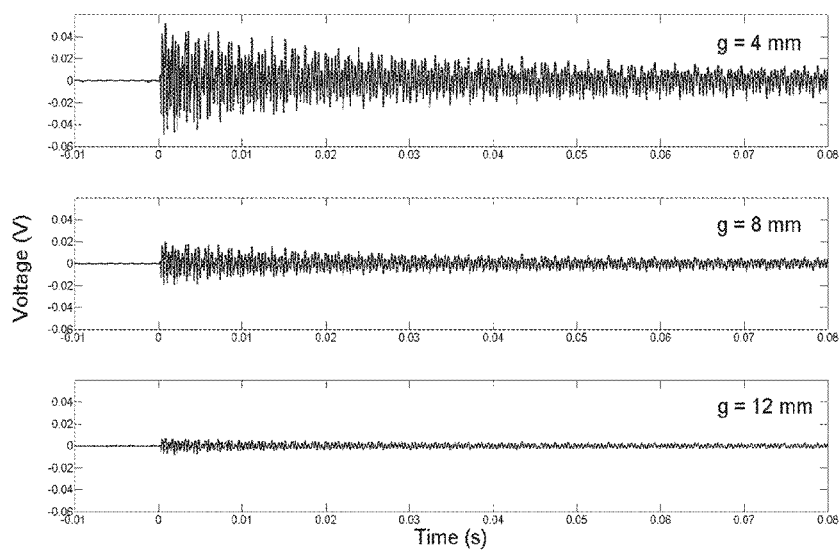
FIG. 8 is an image showing the intensities of output signals of an accelerometer that are detected while vibrating a rod member for different distances between a multi-loop coil and the rod member, in cases where a transducer according to the present embodiment is used as a transmitter.

FIG. 8 is a graph showing the intensities of output signals of an accelerometer that are detected while vibrating a rod member for different distances between a multi-loop coil and the rod member, in cases where a transducer according to the present embodiment is used as a transmitter.

As shown in FIG. 8, as the distance between the multi-loop coil and the rod member increases in the order of 4 mm, 8 mm, and 12 mm, the intensity of the output signal respectively decreases in the order of 0.1013V, 0.0394V, and 0.0150V, respectively. Although the distance may vary based on sensitivity of an accelerometer, the distance between the multi-loop coil and the rod member may be approximately 12 mm to maintain the intensity of a vibration signal at an appropriate level.

Figure 9:
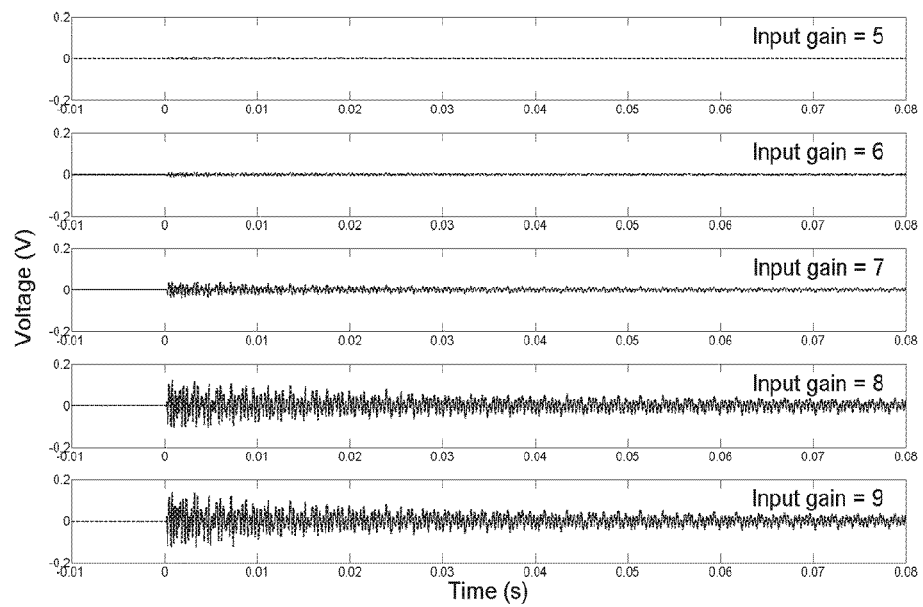
FIG. 9 is an image showing changes in output voltages with respect to the intensities of currents applied to a transducer according to the present embodiment, wherein the transducer is used as a transmitter.

FIG. 9 is a graph showing changes in output voltages with respect to the intensities of currents applied to a transducer according to the present embodiment, wherein the transducer is used as a transmitter.

Currents applied to a multi-loop coil with respect to input gains 5, 6, 7, 8, and 9 were 6.56 A, 9.68 A, 19.06 A, 31.875 A, and 32.188 A, respectively, and output voltages detected by an accelerometer were 0.0078 A, 0.0188V, 0.0813V, 0.2328V, and 0.2641V, respectively.

Figure 10:
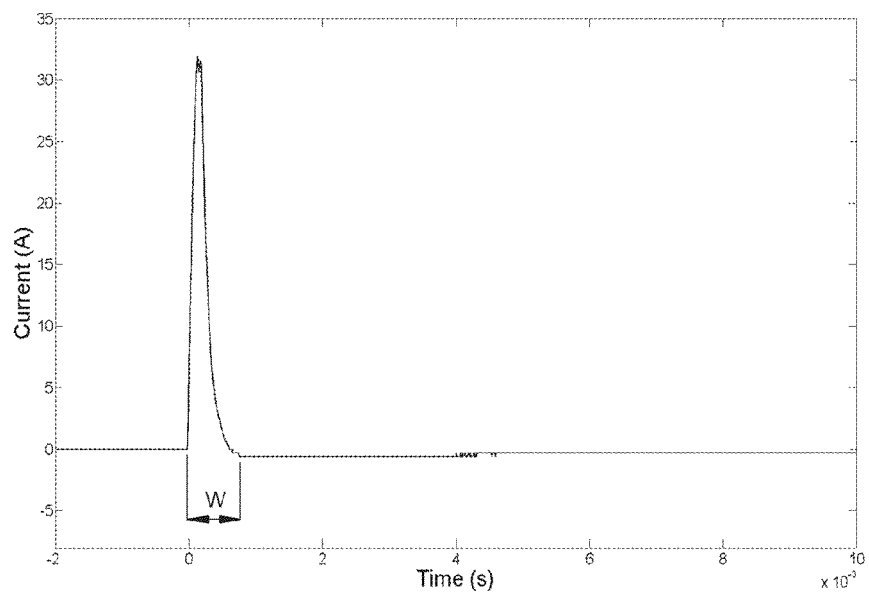
FIG. 10 is an image showing the definition of the impulse width of an input signal.
Figure 11:
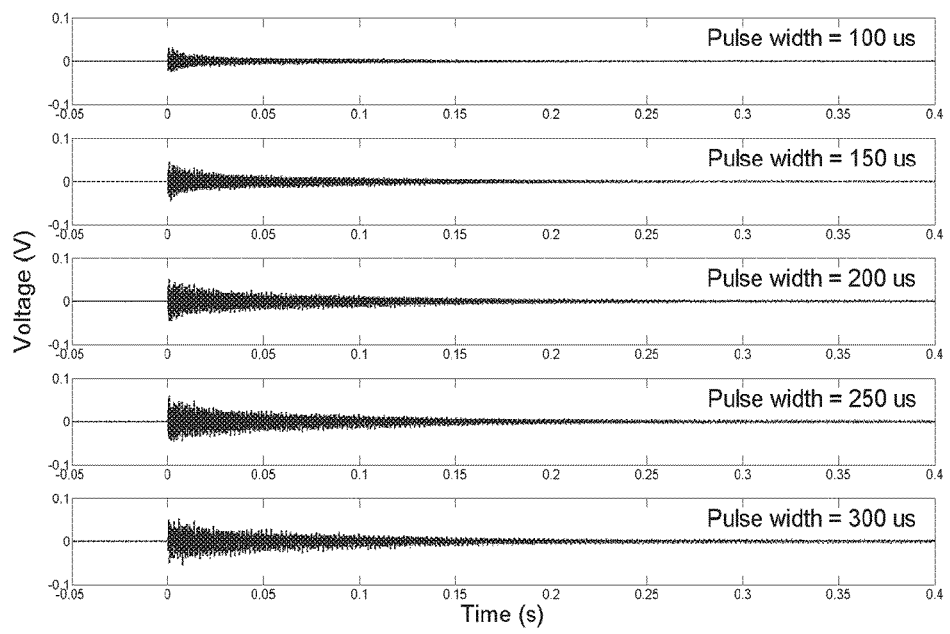
FIG. 11 is an image showing changes in the intensities of output signals according to input widths of input signals.

FIG. 10 is a graph showing the definition of the impulse width of an input signal, and FIG. 11 is a graph showing changes in the intensities of output signals according to input widths of input signals.

As shown in FIG. 10, a time period during which impulse type input signals are applied is indicated by w, and the intensities of output signals are detected for increasing w by steps of 50 μs from 100 μs. As a result, the maximum output signals are detected as shown in Table 1 below.

TABLE 1

| Pulse width (us) | $V_{P-P}^{max}$ (V) |
|---|---|
| 100 | 0.0506 |
| 150 | 0.0725 |
| 200 | 0.0831 |
| 250 | 0.0906 |
| 300 | 0.0893 |

As the width of an input signal increases, more energy is included in a pulse, and thus the intensity of an output signal increases. However, a FRF may be affected on the input signal, that is, a FRF may be affected by the reciprocal of the width of the pulse. For example, when the width of the pulse is 200 μs, a frequency component 5000 Hz (½00 μs) of the width of the pulse may change the FRF. Therefore, when the width of the pulse increases, the reciprocal of the width of the pulse is in a lower frequency domain, and thus the reciprocal of the width of the pulse may overlap a natural frequency. Therefore, the width of an input signal may not be increased unlimitedly to increase the intensity of an output signal, and, if the approximate range of values of the natural frequency of a member to be tested is predictable, the width of an input signal may be set outside the range. Furthermore, in cases where it is difficult to predict the approximate range of values of the natural frequency of a member to be tested, the width of an input signal may be adjusted through repeated experiments, until the frequency component of the input signal and the natural frequency of the member do not overlap.

Figure 12:
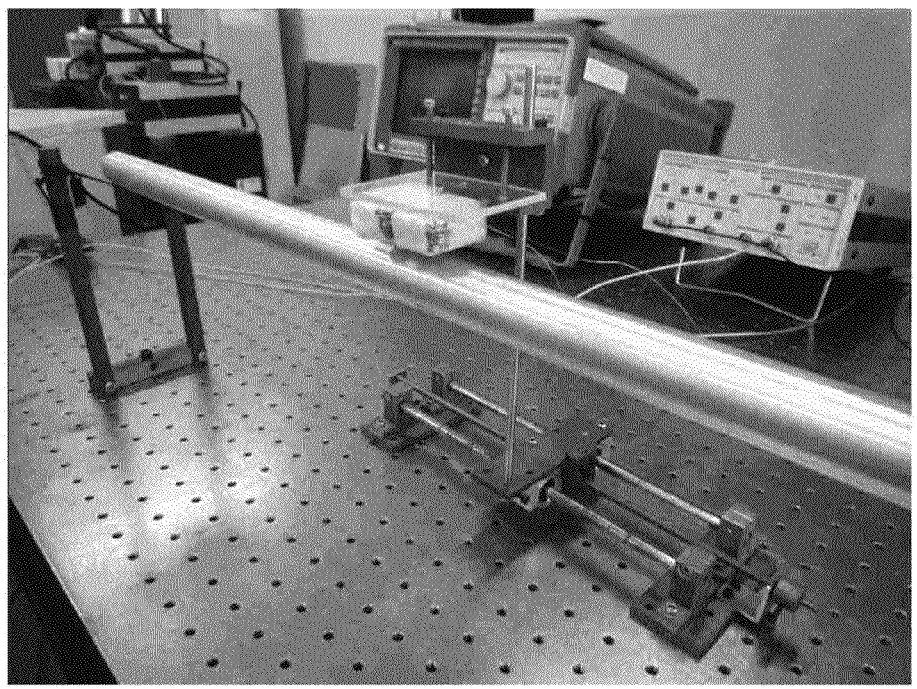
FIG. 12 is a diagram showing an example of installing a transducer according to the present invention apart from a rod member.

FIG. 12 is a diagram showing an example of installing a transducer according to the present invention apart from a rod member.

As shown in FIG. 12, a base is fixed to a surface above which the rod member is located, a column extending adjacent to the rod member is fixed to the base, a plate is fixed onto the top of the column, and a transducer according to the present invention may be installed onto the plate.

Figure 13:
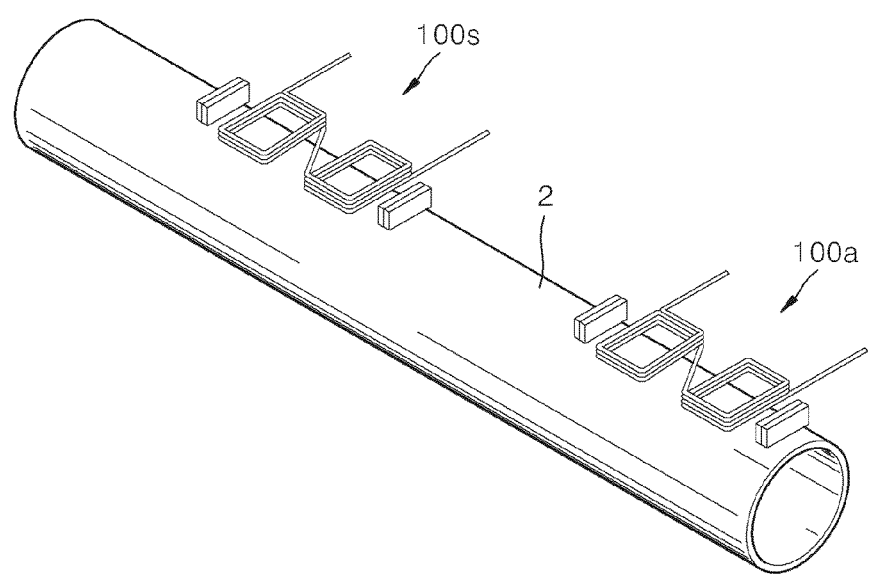
FIG. 13 is a perspective view of a configuration for performing modal testing by using transducers according to the present embodiment, that is, a transmitter 100a and a sensor 100s.

FIG. 13 is a perspective view of a configuration for performing modal testing by using transducers according to the present embodiment, that is. a transmitter 100a and a sensor 100s.

Operations of a transducer according to the present embodiment as a sensor will be described below. The transducer 100a, which is used as a transmitter, vibrates a rod member 2 as described above, and thus the transducer 100a may transmit a wave vibrating in a direction perpendicular to the lengthwise direction of the rod member along the rod member. A static magnetic field that is formed by magnets included in the transducer 100s is formed around the transducer 100s. Furthermore, an electromotive force (EMF) is generated around a multi-loop coil included in the transducer 100s to form a magnetic field, so as to minimize changes in the magnetic field due to subtle deformation of ferromagnetic patch. As a result, a current flows in the multi-loop coil. Vibration transmitted to the rod member may be detected by measuring the EMF.

Meanwhile, as shown in FIG. 13, arrangements of the magnets constituting the static magnetic field forming unit of the present embodiment may vary, and any of various other arrangements are within the scope of the present invention.

In other words, as described above, two magnets may be arranged either inside the multi-loop coil as shown in FIGS. 2 and 4 or outside of the multi-loop coil as shown in FIG. 13. The two magnets may be arranged as shown in FIGS. 2 and 4, in that two opposite poles face each other. Alternatively, the two magnets may be arranged such that neutral portions between the N pole and the S pole of each of the two magnets are parallel to the rod member, that the S pole of one of the magnet faces the rod member, and that the N pole of the other magnet faces the rod member. In other words, the two magnets may be arranged in any of various ways as long as the static magnetic field forming unit forms a magnetic field in the lengthwise direction of the rod member.

Figure 14:
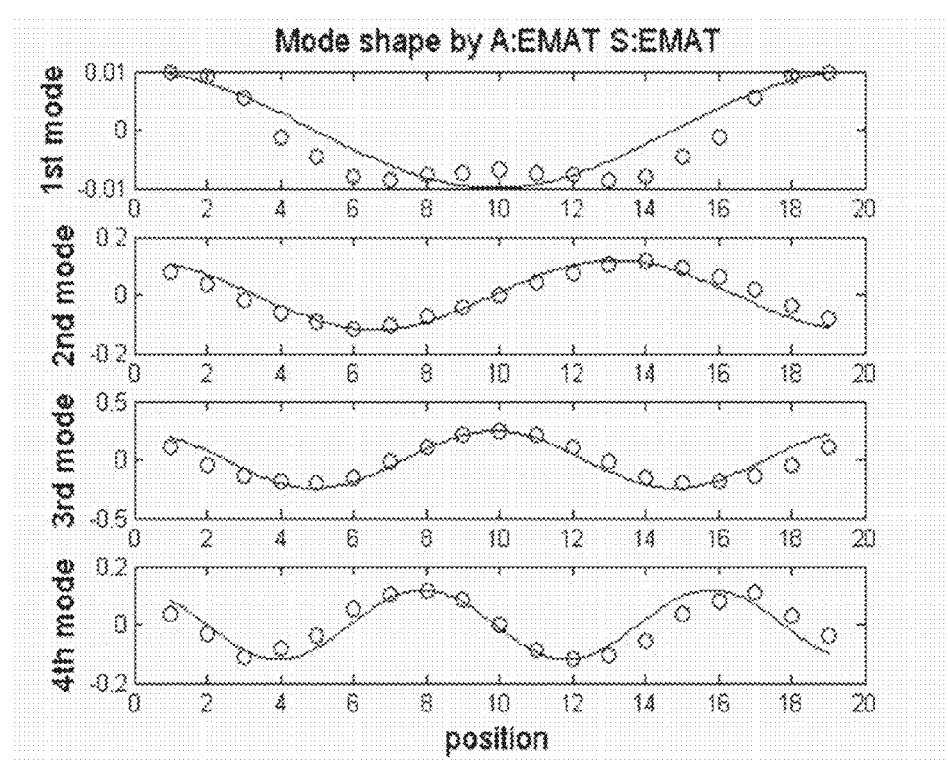
FIG. 14 is a diagram showing a comparison of mode shapes obtained by performing a modal testing by using transducers according to the present embodiment as a transmitter and a sensor versus calculated mode shapes.

FIG. 14 is a diagram showing a comparison of mode shapes obtained by performing a modal testing by using transducers according to the present embodiment as a transmitter and a sensor versus calculated mode shapes.

In FIG. 14, the circles are values detected through an experiment, whereas the solid line indicates the calculated mode shape. As shown in FIG. 14, as a result of performing modal testing with respect to a rod member by using transducers according to the present invention as a transmitter and a sensor, mode shapes that are almost identical to calculated mode shapes can be obtained. Therefore, it is clear that a transducer according to the present invention may excellently function as a transmitter or a sensor.

Meanwhile, the number of windings in a looped coil portion in a multi-loop coil of a transducer according to the present invention may differ between when the corresponding transducer is to be used as a sensor to when the corresponding transducer is to be used as a transmitter. In a transducer according to the present invention, figure-of-8 type coils that are wound the same number of times may be used for both generation and detection of a signal. However, when a transducer according to the present invention is used for generating a signal (a transmitter), it is more efficient to decrease the number of times of winding coils to reduce impedance difference between the transducer and a power amp. On the contrary, when a transducer according to the present invention is used for detecting a signal (a sensor), it is more efficient to increase the number of times of winding coils to increase the sensitivity of the transducer. Therefore, when a device for vibration and diagnosis of a rod member has a configuration in which a transducer according to the present invention is used as a transmitter and another transducer according to the present invention is used as a sensor, the number of winding in the transducer used as the sensor may be greater than the number of winding in the transducer used as the transmitter.

Figure 15:
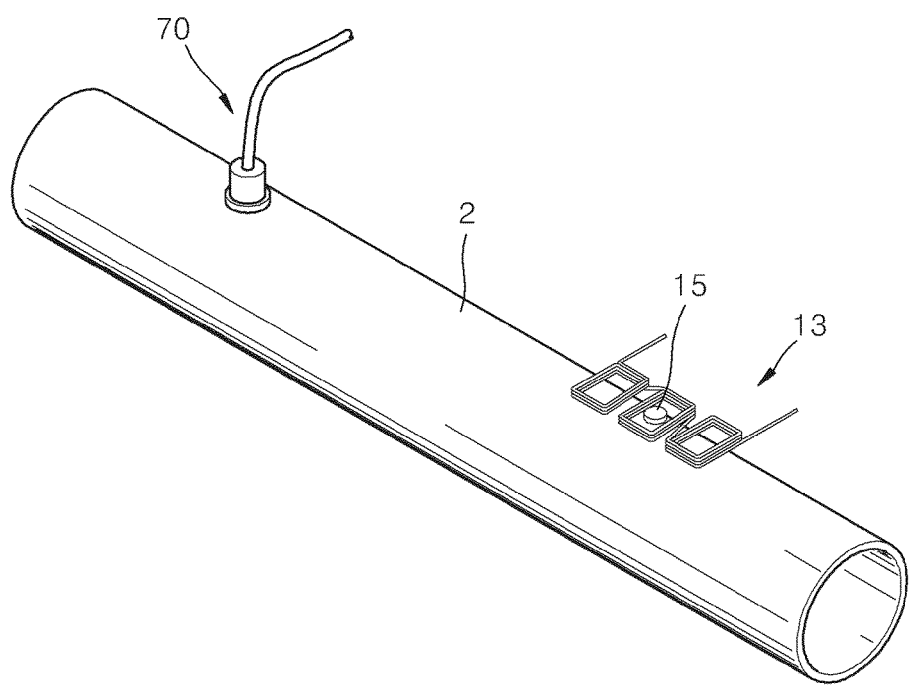
FIG. 15 is a schematic diagram of a transducer according to another embodiment of the present invention.

FIG. 15 is a schematic diagram of a transducer 13 according to another embodiment of the present invention.

As shown in FIG. 15, the transducer according to the present embodiment includes a multi-loop coil that includes three looped coil portions and a magnet 15. The multi-loop coil functions as a dynamic magnetic field forming unit, whereas the magnet functions as a static magnetic field forming unit.

The three looped coil portions are arranged substantially in a line parallel to the lengthwise direction of a rod member 2 to be tested. A direction in which the middle looped coil portion of the three looped coil portions is wound is different from a direction in which the other two looped coil portions are wound.

Figure 16:
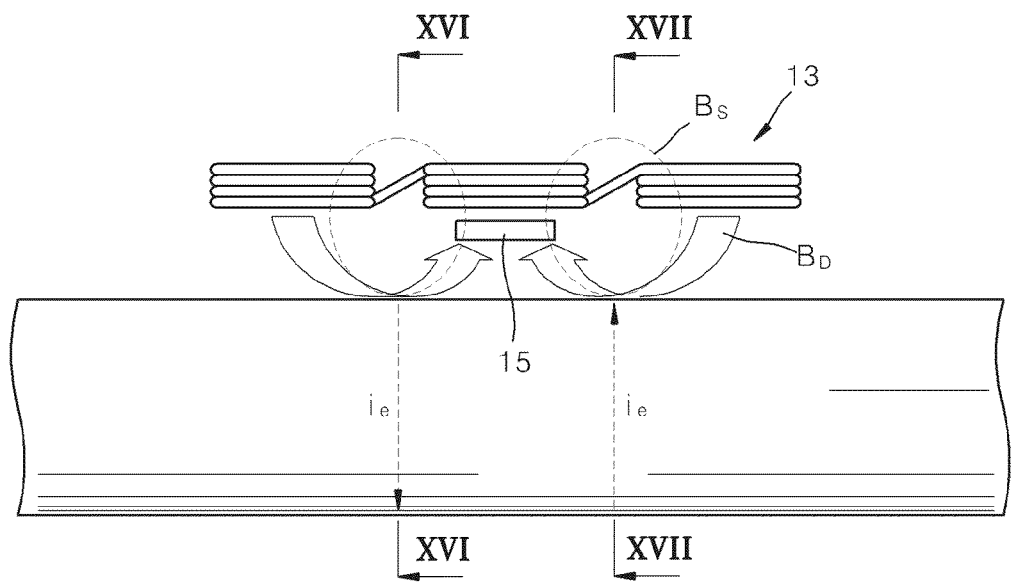
FIG. 16 is a side view of the transducer shown in FIG. 15 for describing operations of the transducer.
Figure 17:
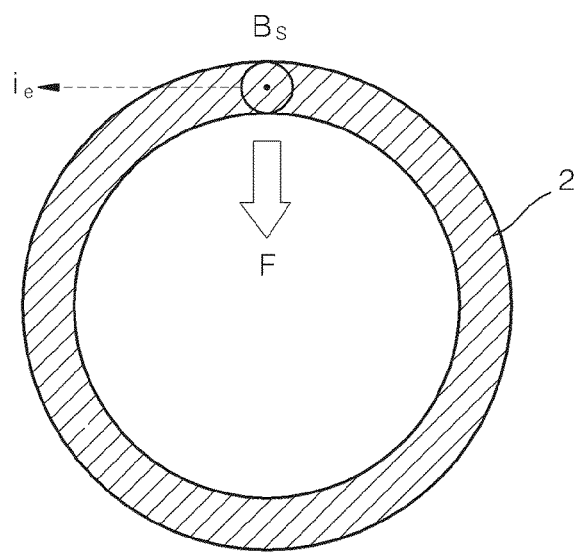
FIG. 17 is a cross-sectional view obtained along a line XVI-XVI of FIG. 16.

FIG. 16 is a side view of the transducer according to the present embodiment shown in FIG. 15 for describing operations of the transducer. FIG. 17 is a cross-sectional view obtained along a line XVI-XVI of FIG. 16, and FIG. 18 is a cross-sectional view obtained along a line XVII-XVII of FIG. 16.

As shown in FIG. 16, when a current flows in a multi-loop coil, a dynamic magnetic field is formed around the multi-loop coil, which may be located close to a pipe, in the direction indicated by an arrow $B_D$ in FIG. 16. Furthermore, a static magnetic field is formed by the magnet in the direction indicated by an arrow $B_S$ in FIG. 16.

Figure 18:
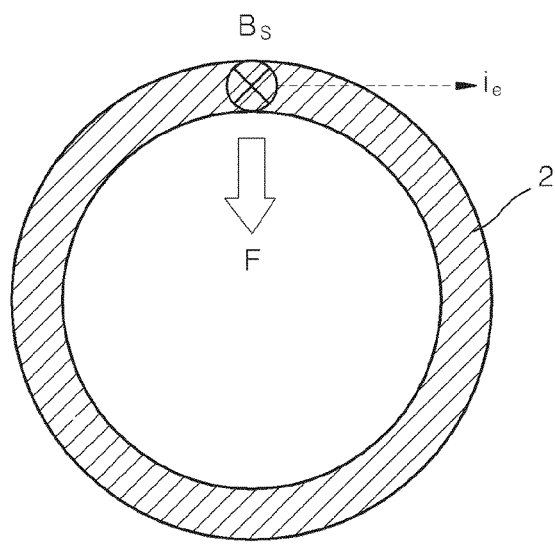
FIG. 18 is a cross-sectional view obtained along a line XVII-XVII of FIG. 16.

Here, when the intensity of the dynamic magnetic field is changed, an eddy current flowing on the surface of a rod member 2 is generated as shown in FIGS. 16 through 18. FIG. 16 shows a case in which the dynamic magnetic field decreases, and an eddy current is formed around the rod member to offset the decrease of the dynamic magnetic field. At this time, Lorentz force is applied to the rod member due to the eddy current and the static magnetic field as shown in FIGS. 17 and 18. The cross-section shown in FIG. 17 and the cross-section shown in FIG. 18 correspond to locations that are equally distant from a magnet 15, where shock forces F may be applied to the rod member at the locations in the same direction perpendicular to the rod member. Therefore, a transducer according to the present embodiment may be used as a transmitter.

Figure 19:
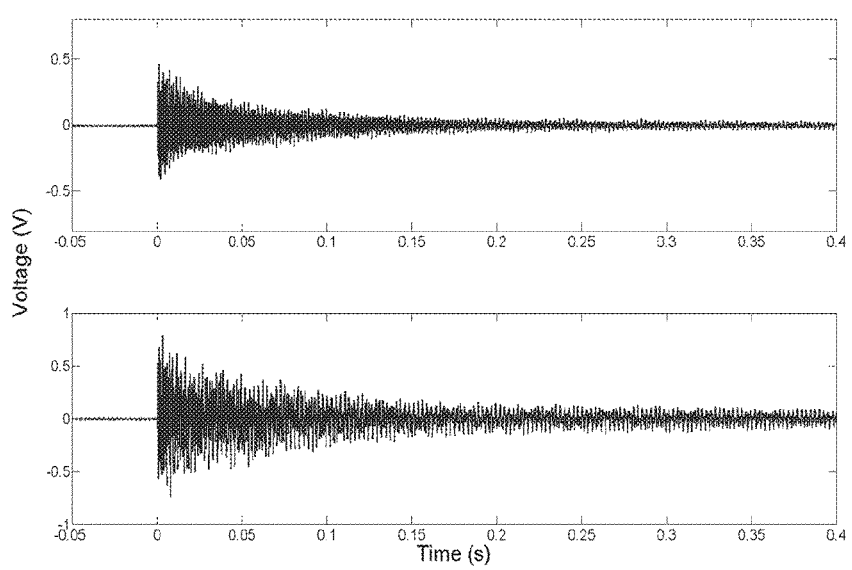
FIG. 19 is an image showing changes in the intensity of output signals with respect to time when a tested component is vibrated by a transducer shown in FIG. 2 or FIG. 15 and the output signal is detected by an accelerometer.

FIG. 19 is a graph showing changes in the intensity of output signals with respect to time when a tested component is vibrated by a transducer according to the previous embodiment of FIG. 2 or the present embodiment of FIG. 15 and the output signal is detected by an accelerometer.

As shown in FIG. 19, if a transducer according to the previous embodiment or the present embodiment is used as a transmitter, an output signal may be obtained by an accelerometer, and thus it is clear that a transducer according to the previous embodiment and the present embodiment may be used as a transmitter for modal testing or a non-destructive diagnosis.

Figure 20:
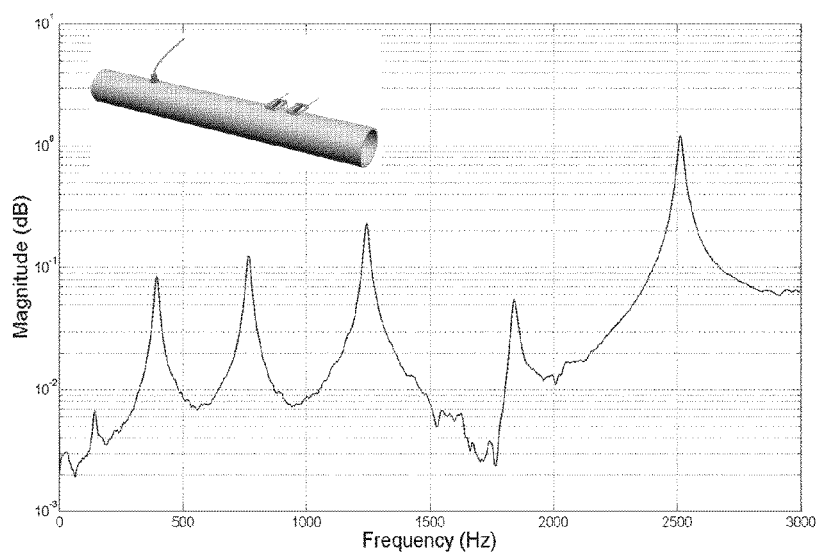
FIG. 20 is an image of a FRF obtained by performing modal testing by using a transducer according to the previous embodiment.
Figure 21:
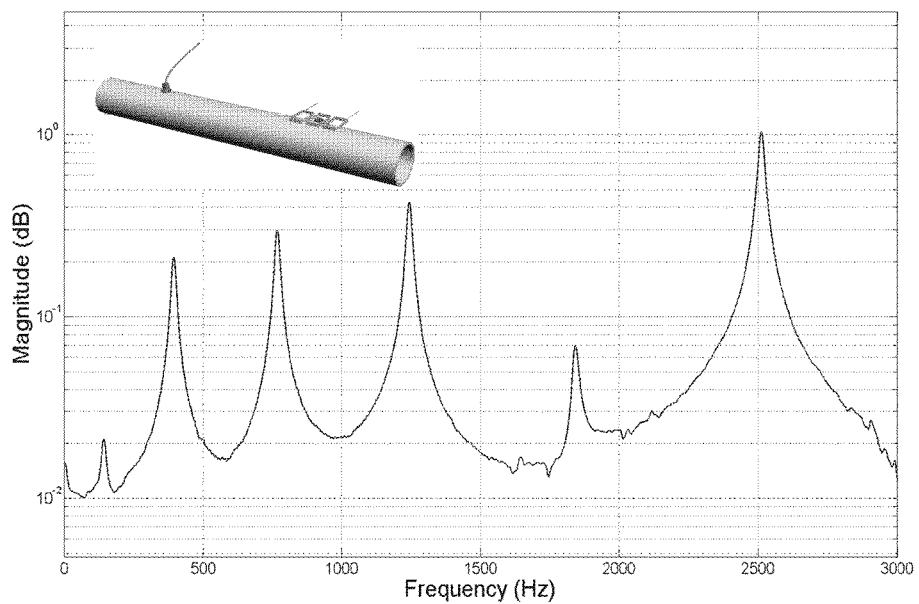
FIG. 21 is an image of a FRF obtained by performing modal testing by using a transducer according to the present embodiment.

FIG. 20 is a graph of a FRF obtained by performing modal testing by using a transducer according to the previous embodiment, and FIG. 21 is a graph of a FRF obtained by performing modal testing by using a transducer according to the present embodiment.

As shown in FIGS. 20 and 21, a natural frequency belonging to a low frequency domain under 500 Hz may be detected even when a transducer according to the previous embodiment or the present embodiment is used as a transmitter, and thus it is clear that a transducer according to the previous embodiment and the present embodiment may be used as a transmitter.

Meanwhile, a transducer according to the present invention as described above may not only be applied to a conductive rod member in which an eddy current may flow, but also may be applied a non-conductive rod member when a conductive foil is attached to surround the surface of a portion in which a transducer is located.

Figure 22:
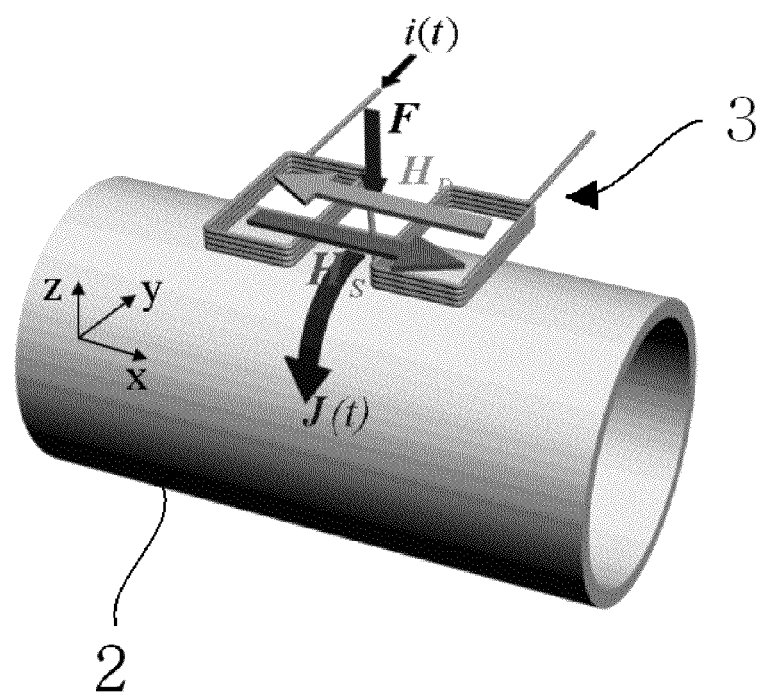
FIG. 22 is a diagram showing a configuration of a transducer according to another embodiment of the present invention.

FIG. 22 is a diagram showing a configuration of a transducer according to another embodiment of the present invention.

As shown in FIG. 22, the difference between the transducer according to the present embodiment and the transducers according to the previous embodiments is that, the transducer according to the present embodiment includes no static magnetic field forming unit and a magnetic field is formed only by a dynamic magnetic field forming unit. That is to say, the transducer according to the present embodiment comprises a multi-loop coil and a power source. The multi-loop coil includes two or more looped coil portions that are connected to each other, wherein the looped coil portions are located on top of a target rod member. The power source applies power to the multi-loop coil, so that the multi-loop coil forms a magnetic field on the surface of the rod member in a direction parallel to the lengthwise direction of the rod member.

After the transducer of FIG. 22, which includes a figure-of-8 type coil as a dynamic magnetic field forming unit, is arranged to be a predetermined distance apart from the target rod member and current flowing in the figure-of-8 type coil is changed, an eddy current flows along the outer perimeter of the rod member, and force is applied to the rod member by the eddy current and the magnetic field formed by the dynamic magnetic field forming unit according to the Lorenz's law. The mechanism of the force application may be logically described as below.

In FIG. 2 and FIG. 15, Magnetic flux density formed by the figure-of-8 type coil, which is the dynamic magnetic field forming unit, and a magnet, which is a static magnetic field forming unit, may be expressed as shown below in Equation 1.

$$B = B^S + B^D = \mu_0 \mu_r H^S + \mu_0 \mu_r H^D \quad \text{[Equation 1]}$$

Here, B denotes overall magnetic flux density, $B^S$ denotes static magnetic flux density, $B^D$ denotes dynamic magnetic flux density, $\mu_0$ denotes free-space permeability, $\mu_r$ denotes relative permeability, $H^S$ denotes static magnetic field, and $H^D$ denotes dynamic magnetic field.

If it is assumed that electromagnetic field is changed on the x-z plane, the current density $J_y$ of eddy current generated by a rod member, which is a conductor, may be expressed as shown below in Equation 2.

$$J_y = \frac{\partial H_x^D}{\partial z} - \frac{\partial H_z^D}{\partial x} \quad \text{[Equation 2]}$$

In the configuration as shown in FIG. 2 and FIG. 15, variations of variables in the z-axis direction are significantly smaller than variations of the variables in the x-axis direction, and thus the magnitude of Lorenz's force in the z-axis direction may be expressed as shown below in Equation 3.

$$F_z = -(B_x^S + B_x^D)\frac{\partial H_x^D}{\partial z} = -(\mu_0 \mu_r H_x^S + \mu_0 \mu_r H_x^D)\frac{\partial H_x^D}{\partial z} \quad \text{[Equation 3]}$$

Here, in the case where no permanent magnet exists as shown in FIG. 22, $B^S$ is omitted. Therefore, the magnitude of Lorenz's force applied in the embodiment shown in FIG. 22 may be expressed as shown below in Equation 4.

$$F_z = -(B_x^D)\frac{\partial H_x^D}{\partial z} = -(\mu_0 \mu_r H_x^D)\frac{\partial H_x^D}{\partial z} \quad \text{[Equation 4]}$$

As shown in Equation 4, a rod member may also be vibrated according to the mechanism of electromagnetic acoustic transducer in the present embodiment without a static magnetic field unlike in the previous embodiments. However, in the case where a static magnetic field exists as shown in FIG. 2 and FIG. 15, additional force due to the static magnetic field will be applied, and thus the rod member may be vibrated with greater force.

Figure 23:
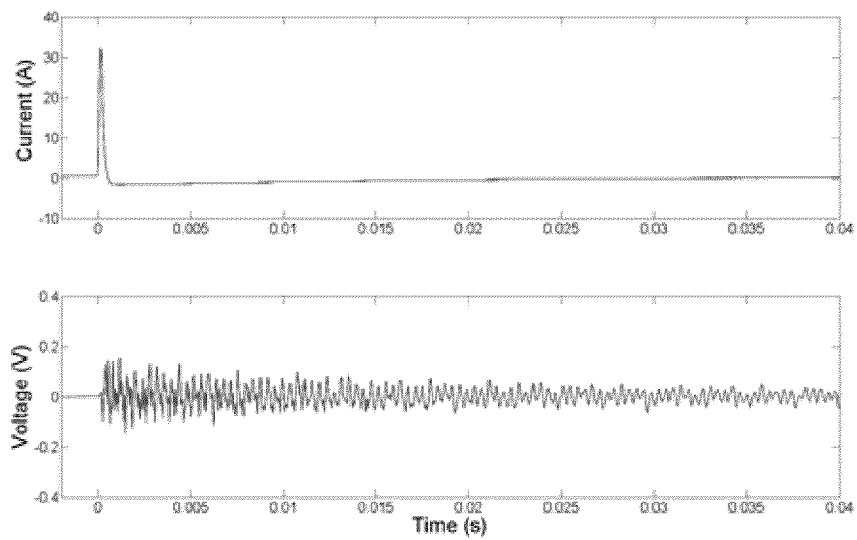
FIG. 23 is an image showing input currents at a multi-loop coil and output currents at an accelerometer in case of vibrating an aluminum pipe by using the transducer shown in FIG. 22.
Figure 24:
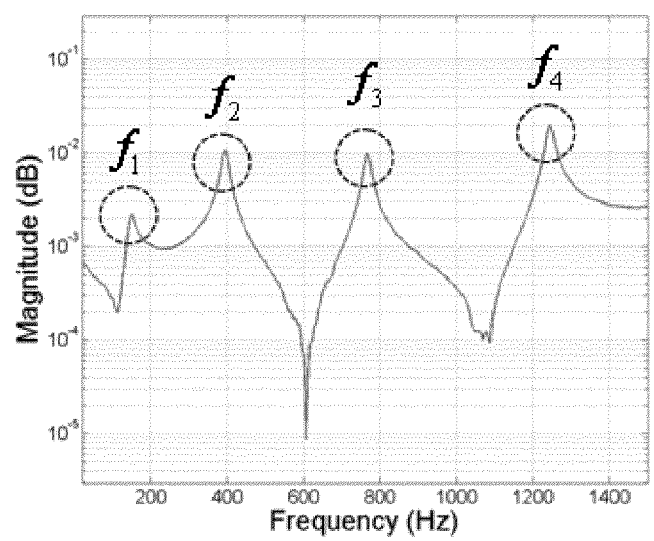
FIG. 24 is an image of a frequency response function obtained in the experiment of FIG. 23.
Figure 25:
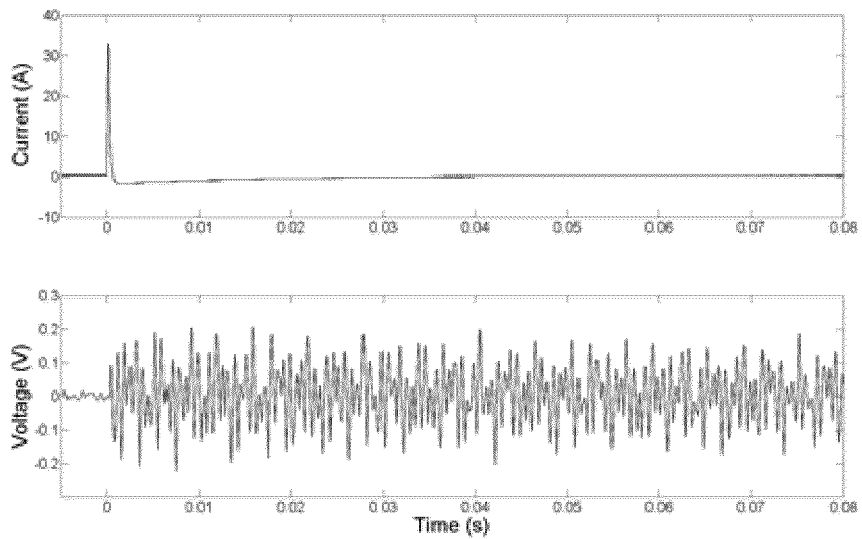
FIG. 25 is an image showing input currents at a multi-loop coil and output currents at an accelerometer in case of vibrating a steel pipe by using the transducer shown in FIG. 22.
Figure 26:
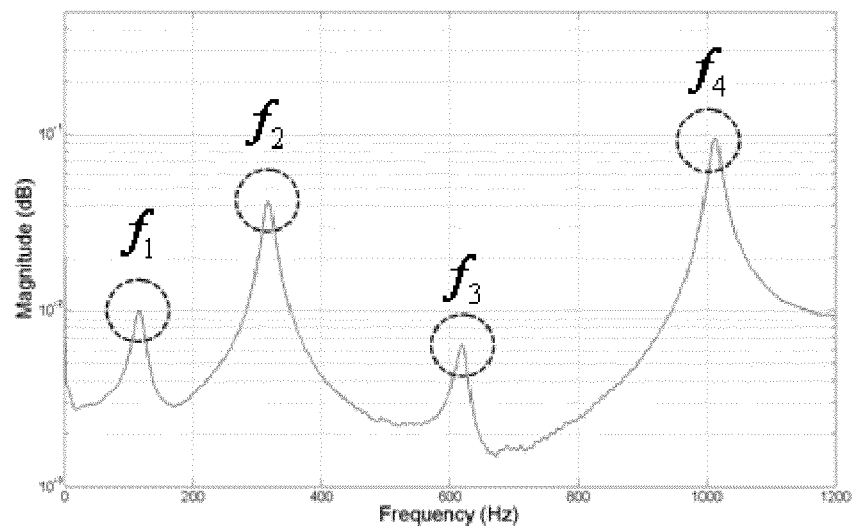
FIG. 26 is an image of a frequency response function obtained in the experiment of FIG. 25.

FIG. 23 is a graph showing input currents at a multi-loop coil and output currents at an accelerometer in case of vibrating an aluminum pipe by using the transducer according to the embodiment shown in FIG. 22, FIG. 24 is a graph of a frequency response function obtained in the experiment of FIG. 23, FIG. 25 is a graph showing input currents at a multi-loop coil and output currents at an accelerometer in case of vibrating a steel pipe by using the transducer according to the embodiment shown in FIG. 22, and FIG. 26 is a graph of a frequency response function obtained in the experiment of FIG. 25.

In the experiments of FIGS. 23 and 24, an aluminum pipe, which has the length of 1000 mm, the outer diameter of 25 mm, and the thickness of 2.0 mm, and all four points indicated as peaks in the frequency response function shown in FIG. 24 correspond to the unique vibration frequency of the tested aluminum pipe. In the experiments of FIGS. 25 and 26, a steel pipe, which has the length of 1000 mm, the outer diameter of 19 mm, and the thickness of 2.0 mm, and all four points indicated as peaks in the frequency response function shown in FIG. 26 correspond to the unique vibration frequency of the tested steel pipe.

Furthermore, although only the case in which the multi-loop coil is figure-of-8 type (having two looped-coils) is described above with reference to FIGS. 22 through 26, the general mechanism of the embodiment shown in FIG. 22, which may be expressed by Equation 1 through 4, may also be applied to a case with more looped-curves.

Furthermore, when a rod member to be vibrated is not a conductor, if a conductive foil is attached onto the surface of the rod member, the rod member may be vibrated like as a conductive rod member, based on the mechanism of the embodiment shown in FIG. 22.

According to a non-contact type transducer according to the embodiments of the present invention as described above, modal testing may be performed by a person with relatively high precision. Furthermore, a non-contact type structural diagnosis may be easily performed with respect to any component by using a non-contact type transducer according to the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A transducer comprising:
   a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member; and
   one or more magnets that are arranged to form a static magnetic field on the surface of the rod member, whereon the surface of the rod member a dynamic magnetic field is formed by the multi-loop coils in the direction parallel to the lengthwise direction of the rod member, even partially in a direction parallel to the lengthwise direction of the rod member,
   wherein the rod member is formed of a conductor,
   an eddy current flowing on the surface of the rod member in a circumferential direction of the rod member is generated by adjusting currents flowing in the multi-loop coils,
   a force is applied to the rod member in a direction perpendicular to the lengthwise direction of the rod member due to the static magnetic field formed by the eddy current and the static magnetic field,
   when a wave vibrating in a direction perpendicular to the lengthwise direction of the rod member is transmitted along the rod member, an eddy current is generated in the circumferential direction of the rod member under the static magnetic field, and an electromotive force is formed in the multi-loop coil to form a magnetic field in a direction that is opposite to the direction in which a magnetic field formed by the eddy current is formed, to offset the magnetic field formed by the eddy current, and a vibration transmitted to the rod member is detected by detecting the electromotive force.

2. The transducer of claim 1, wherein the multi-loop coil is a figure-of-8 type coil comprising two looped coil portions,
   the two looped coil portions are arranged on top of the rod member in a line parallel to the lengthwise direction of the rod member, and
   directions in which the two looped coil portions are wound are different from each other.

3. The transducer of claim 1, wherein the multi-loop coil comprises three looped coil portions,
   the three looped coil portions are arranged on top of the rod member in a line parallel to the lengthwise direction of the rod member, and
   a direction in which a middle looped coil portion of the three looped coil portions is wound is different from a direction in which the other two looped coil portions are wound.

4. The transducer of claim 3, wherein the magnet is arranged at a center of the middle looped coil portion of the three looped coil portions and apart from the rod member, and
   a neutral plane between the N pole and the S pole of the magnet is parallel to the rod member.

5. The transducer of claim 1, wherein the static magnetic field is formed by arranging two or more magnets such that opposite poles thereof face each other and the magnets are apart from each other in the lengthwise direction of the rod member.

6. The transducer of claim 1, wherein the static magnetic field is formed by two magnets, and
   the two magnets are arranged such that neutral planes between the N poles and the S poles of the two magnets are parallel to the rod member, such that the S pole of one of the magnet faces the rod member, and such that the N pole of the other magnet faces the rod member.

7. A transducer comprising:
   a multi-loop coil including two or more looped coil portions that are connected to each other, wherein the looped coil portions are located on top of a rod member, and the looped coil portions form magnetic fields on the surface of the rod member in a direction parallel to the lengthwise direction of the rod member;
   one or more magnets that are arranged to form a static magnetic fields on the surface of the rod member, whereon the surface of the rod member a dynamic magnetic field is formed by the multi-loop coils in a direction parallel to the lengthwise direction of the rod member, even partially in a direction parallel to the lengthwise direction of the rod member; and
   a conductive foil wound around the rod member to cover portions of the rod member facing the multi-loop coils,
   wherein an eddy current flowing on the surface of the rod member in the circumferential direction of the rod member is generated by adjusting currents flowing in the multi-loop coils,
   a force is applied to the rod member in a direction perpendicular to the lengthwise direction of the rod member due to the static magnetic field formed by the eddy current and the static magnetic field,
   when a wave vibrating in a direction perpendicular to the lengthwise direction of the rod member is transmitted along the rod member, an eddy current is generated in the circumferential direction of the rod member under the static magnetic field, and an electromotive force is formed in the multi-loop coil to form a magnetic field in a direction that is opposite to the direction in which a magnetic field formed by the eddy current is formed, to offset the magnetic field formed by the eddy current, and
a vibration transmitted to the rod member is detected by detecting the electromotive force.

8. The transducer of claim 7, wherein the multi-loop coil is a figure-of-8 type coil comprising two looped coil portions,
the two looped coil portions are arranged on top of the rod member in a line parallel to the lengthwise direction of the rod member, and
directions in which the two looped coil portions are wound are different from each other.

9. The transducer of claim 7, wherein the multi-loop coil comprises three looped coil portions,
the three looped coil portions are arranged on top of the rod member in a line parallel to the lengthwise direction of the rod member, and
a direction in which a middle looped coil portion of the three looped coil portions is wound is different from a direction in which the other two looped coil portions are wound.

10. The transducer of claim 9, wherein the magnet is arranged at a center of the middle looped coil portion of the three looped coil portions and apart from the rod member, and
a neutral plane between the N pole and the S pole of the magnet is parallel to the rod member.

11. The transducer of claim 7, wherein the static magnetic field is formed by arranging two or more magnets such that opposite poles thereof face each other and the magnets are apart from each other in the lengthwise direction of the rod member.

12. The transducer of claim 7, wherein the static magnetic field is formed by two magnets, and
the two magnets are arranged such that neutral planes between the N poles and the S poles of the two magnets are parallel to the rod member, such that the S pole of one of the magnet faces the rod member, and such that the N pole of the other magnet faces the rod member.

13. A transducer comprising:
a multi-loop coil including two or more looped coil portions that are connected to each other, wherein the looped coil portions are located on top of a rod member, one or more of the looped coil portions have opposite winding direction to the others to make opposite magnetic field directions, and the looped coil portions form magnetic fields on the surface of the rod member in a direction parallel to the lengthwise direction of the rod member; and
a power source, which applies power to the multi-loop coil, so that the multi-loop coil forms a magnetic field,
wherein the rod member is formed of a conductor,
an eddy current flowing on the surface of the rod member in the circumferential direction of the rod member is generated by adjusting currents flowing in the multi-loop coils, and
a force is applied to the rod member in a direction perpendicular to the lengthwise direction of the rod member due to the magnetic field formed by the eddy current and the magnetic field formed by the multi-loop coil according to Lorenz's law.

14. The transducer of claim 13, wherein the multi-loop coil is a figure-of-8 type coil comprising two looped coil portions,
the two looped coil portions are arranged on top of the rod member in a line parallel to the lengthwise direction of the rod member, and
directions in which the two looped coil portions are wound are different from each other.

15. The transducer of claim 13, wherein the multi-loop coil comprises three looped coil portions,
the three looped coil portions are arranged on top of the rod member in a line parallel to the lengthwise direction of the rod member, and
a direction in which a middle looped coil portion of the three looped coil portions is wound is different from a direction in which the other two looped coil portions are wound.

16. A transducer comprising:
a multi-loop coil including two or more looped coil portions that are connected to each other, wherein the looped coil portions are located on top of a rod member, one or more of the looped coil portions have opposite winding direction to the others to make opposite magnetic field directions, and the looped coil portions form magnetic fields on the surface of the rod member in a direction parallel to the lengthwise direction of the rod member;
a power source, which applies power to the multi-loop coil, so that the multi-loop coil forms a magnetic field; and
a conductive foil wound around the rod member to cover portions of the rod member facing the multi-loop coils,
wherein an eddy current flowing on the surface of the rod member in the circumferential direction of the rod member is generated by adjusting currents flowing in the multi-loop coils, and
a force is applied to the rod member in a direction perpendicular to the lengthwise direction of the rod member due to the static magnetic field formed by the eddy current and the static magnetic field according to Lorenz's law.

17. The transducer of claim 16, wherein the multi-loop coil is a figure-of-8 type coil comprising two looped coil portions,
the two looped coil portions are arranged on top of the rod member in a line parallel to the lengthwise direction of the rod member, and
directions in which the two looped coil portions are wound are different from each other.

18. The transducer of claim 16, wherein the multi-loop coil comprises three looped coil portions,
the three looped coil portions are arranged on top of the rod member in a line parallel to the lengthwise direction of the rod member, and
a direction in which a middle looped coil portion of the three looped coil portions is wound is different from a direction in which the other two looped coil portions are wound.

* * * * *